United States Patent [19]

Chu et al.

[11] 4,309,342

[45] Jan. 5, 1982

[54] ANTIBACTERIAL PEPTIDES

[75] Inventors: Daniel T. Chu, Lake Villa; Jerry R. Martin, Waukegan; Alford M. Thomas, Wadsworth, all of Ill.

[73] Assignee: Abbott Laboratories, North Chicago, Ill.

[21] Appl. No.: 165,583

[22] Filed: Jul. 3, 1980

[51] Int. Cl.$^3$ .................... C07C 103/52; A61K 31/42; A61K 31/195; C12P 13/06

[52] U.S. Cl. .................... 260/112.5 R; 424/272; 424/319; 435/116

[58] Field of Search ............... 424/272, 319; 435/116; 260/112.5 R

[56] References Cited

U.S. PATENT DOCUMENTS

| | | | |
|---|---|---|---|
| 3,929,576 | 12/1975 | Reinhold | 435/116 |
| 3,956,367 | 5/1976 | Kollonitsch | 424/319 |
| 4,031,231 | 6/1977 | Kahan | 424/272 |
| 4,119,620 | 10/1978 | Nagatsu et al. | 260/112.5 R |
| 4,176,116 | 11/1979 | Hassall et al. | 260/112.5 R |
| 4,187,216 | 2/1980 | Hassall et al. | 260/112.5 R |

FOREIGN PATENT DOCUMENTS

| | | | |
|---|---|---|---|
| 270399 | 11/1963 | Australia | 424/177 |
| 269188 | 1/1965 | Australia | 424/177 |
| 272332 | 4/1965 | Australia | 424/177 |

OTHER PUBLICATIONS

Pettit, Synthetic Peptides, vol. I, 81–82.
Pettit, Synthetic Peptides, vol. 5, 136.
Chem. Abstr., vol. 79, 1973, p. 115887t.
Chem. Abstr., vol. 83, 1975, p. 84873m.
Chem. Abstr., 84, 1974, p. 106072z.

*Primary Examiner*—Delbert R. Phillips
*Attorney, Agent, or Firm*—Robert L. Niblack; Paul D. Burgauer

[57] ABSTRACT

It has been found that dipeptides containing a 3-fluoro-D-alanine N-terminus are powerful antibacterials and produce a highly useful synergistic effect with antibiotics.

8 Claims, No Drawings

ANTIBACTERIAL PEPTIDES

DETAILED DESCRIPTION OF THE INVENTION

As micro-organisms become resistant to known antibiotics, continued effort is needed to find new compounds or combinations of compounds which effectively inhibit bacterial growth.

It has now been found that a peptide of the formula

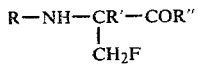

wherein the shown aminoacid is in the D-configuration, R is hydrogen or an easily removable protective group, R' is hydrogen or deuterium and R" is the imino moiety of an α-aminoacid in the L-configuration, the corresponding loweralkyl esters thereof, or nontoxic acid addition salts thereof, are useful antibacterials; they also represent powerful syngerists for D-cylcloserine and other antibiotics.

The amino group substituent R particularly includes an acyl group of a lower fatty acid such as acetyl, propionyl, isobutyryl and the like. The above moiety R" particularly represents the known, protein-derived aminoacids, including glycine which, of course, does not have a chiral center. The definition also includes other aminoacids where the amino group is attached to the 2- or α-position of the acid. The protein-derived aminoacid may be represented by leucine, valine, norvaline, proline, serine, tyrosine, alanine, phenylalanine, threonine, methionine, glutamine, histidine, arginine, lysine and tryptophane. The new dipeptides have the unnatural sequence of a (deuterated) D-β-fluoroalanine coupled to an L-aminoacid. Such a D-L sequence is usually restricted to the cell wall components of microorganisms and its antibacterial activity is completely unexpected.

The new dipeptide can easily be synthesized by coupling, in well known fashion, the active ester of an N-protected β-fluoro-D-alanine (or its deuterated analog) with an aminoacid in the L-configuration. Among the active esters, the hydroxysuccinimide, pentachlorophenyl, 4-nitrophenyl, 2,4,5-trichlorophenyl, a fluorophenyl, N-hydroxyisobornyldicarboximide or similarly familiar esters of N-protected β-fluoro-D-alanine can be used for the coupling reaction. The $N^\alpha$-group and any sensitive functional group in the aminoacid moiety represented by R" above can be protected with the usual well-known groups that can subsequently be removed by a mild chemical reaction which does not affect the peptide bond formed. Among the groups frequently used as temporary protection are the carbobenzoxy (hereinafter identified as Z) or the tert. butoxycarbonyl for amino groups, particularly the $N^\alpha$-group, while benzyl or other moieties can be used to protect the hydroxy groups in serine, tyrosine or hydroxyproline or the imidazole group of histidine. Hydrogenation will remove said benzyl group after the peptide coupling has been effected and treatment with hydrobromic acid or hydrofluoric acid will remove other protective groups used by the skilled artisan, without cleaving the peptide bond. The free acid can be converted into the desired alkyl ester in known fashion and/or the $N^\alpha$-group can be acylated in known manner. The identical reaction sequence can also be used when the starting material is the 2-deuterated 3-fluoro-D-alanine.

In order to illustrate the preparation of the new peptide, reference is made to the following examples which, however, are not intended to limit this invention in any respect. In all examples, the optical rotations were taken at 25° C. (unless shown differently) in 1 N HCl at the concentrations given.

EXAMPLE 1

A stirred solution of 965 mg. of N-carbobenzoxy-β-fluoro-D-alanine and 506 mg. of N-hydroxysuccinimide in 15 ml. of 1,2-dimethoxyethane (DME) was cooled in an ice bath and treated with 908 mg. of dicyclohexylcarbodiimide. After stirring for 2 hours at ice bath temperature, and 1 hour at room temperature, 10 ml. of DME was added and the slurry was filtered directly into a solution of 445 mg. of L-alanine and 840 mg. of sodium bicarbonate in 25 ml. of water. After stirring overnight, the solution was concentrated to a thick oil which was acidified with 1 N-hydrochloric acid. This mixture was stirred in an ice bath for 7 hours, producing a white, amorphous solid which was collected by filtration, washed with ice water and dried to give 850 mg. of N-carbobenzoxy-β-fluoro-D-alanyl-L-alanine.

Hydrogenation of this product in 100 ml. of methanol in the presence of 0.2 g. of 5% Pd-on-carbon gave, after filtration and solvent evaporation, 278 mg. of β-fluoro-D-alanyl-L-alanine as an amorphous powder; $[\alpha]^{20}+56.6°$ (C, 1.1).

EXAMPLE 2

By substituting the L-alanine of Example 1 with 826 mg. of L-phenylalanine, the above process produces 290 mg. of β-fluoro-D-alanyl-L-phenylalanine as an amorphous solid; $[\alpha]^{20}+5.5°$ (C, 0.2).

EXAMPLE 3

By substituting the L-alanine of Example 1 with 1.19 g. of γ-benzylglutamic acid, the described procedure gives 480 mg. of βF-D-Ala-L-Glu; $[\alpha]_D+32°$ (C, 1.0).

EXAMPLE 4

In the fashion described above, 650 mg. of L-leucine is converted to 175 mg. of F-D-Ala-L-Leu; $[\alpha]_D+29°$ (C, 1.0) an an amorphous powder after passing it through a Sephadex ® column using water as eluent.

EXAMPLE 5

The process of Example 1 used with 1.03 g. of 2-aminoisobutyric acid produced 120 mg. of βF-D-Ala-Aibu; $[\alpha]_D+4.5°$ (C, 1.0).

EXAMPLE 6

The process of Example 4 used with 560 mg. of valine produced 100 mg. of βF-D-Ala-L-Val, $[\alpha]_D+10°$ (C, 0.5).

When the L-aminoacids in the above examples are replaced by the corresponding known loweralkyl esters, i.e., leucyl methyl ester, valine butyl ester, and alanyl ethyl ester, the corresponding D-L-dipeptide loweralkyl esters are obtained in the same fashion.

By using the deuterated βF-D-Ala-2-d (made according to the method of Dolling et al., J. Org. Chem., 43, 1634 of 1978) in the process of Example 1, βF-D-Ala-2-d-L-Ala is obtained in similar yield.

Other compounds of the above general description can easily be made by repeating Example 1 but using other protective groups for βF-D-Ala or βF-D-Ala-2-d, other active esters thereof or other L-aminoacids. For instance, if said L-aminoacid is isoleucine or α-aminocaproic acid, the corresponding compounds are obtained where R represents L-isoleucyl or L-α-aminocaproyl. Obviously, other amino acids carrying protected additional functional groups can be employed to make the dipeptides of the current invention. Particularly, (deuterated) β-fluoro-D-alanyl- L-threonine, L-tryptophane, and -L-tyrosine can be made by the above route. In these and other instances, functional groups where present, can be temporarily protected in known fashion by benzyl, carbobenzyloxy, tert. butyl or other protective groups commonly used in the peptide art.

EXAMPLE 7

The above fluorinated dipeptides are prepared in sterile concentrated aqueous solutions. Serial dilutions are made to give a range of concentrations of the test substances. Samples of the dilutions are mixed with an appropriate sterile synthetic bacterial growth medium in test tubes. The tubes are then inoculated with an appropriate test organism and incubated at 35°–37° C. for 16–20 hours. Minimum inhibitory concentrations, i.e., that concentration which inhibits visible growth, are shown in Table I. Where the results are shown in parentheses, a higher concentrations did not always inhibit organism growth. The organisms used in this test were as follows:

TABLE I

| | |
|---|---|
| I | *Staph. aureus* Smith |
| II | *Strep. faecalis* 10541 |
| III | Enterococcus 89 |
| IV | *Bacillus subtilis* 9466 |
| V | *E. coli* Juhl |
| VI | *Kleb. pneumonise* 8045 |
| VII | *Shigella sonnei* 9290 |

| Example No. | 1 | 2 | 3 | 4 | 5 | 6 |
|---|---|---|---|---|---|---|
| I | (25) | (3.1) | 800 | 800 | 800 | 800 |
| II | (1.56) | 0.78 | 50 | 3.1 | 800 | (6.2) |
| III | 200 | 25 | 25 | 25 | 25 | 6.2 |
| IV | (.78) | 3.1 | 3.1 | 6.2 | (25) | (3.1) |
| V | (.78) | (6.2) | (12.5) | 800 | (12.5) | 800 |
| VI | (12.5) | (12.5) | (25) | 800 | 800 | 800 |
| VII | (.39) | (1.56) | (12.5) | 800 | (6.2) | (25) |

EXAMPLE 8

The in vivo activity of the fluorinated dipeptides and the fluorinated dipeptide-antibiotic combinations provided by the present invention were demonstrated as follows:

Charles River mice weighing approximately 20 g. each, were infected intraperitoneally with 10–100 times the $LD_{50}$ of the infecting organism. At predetermined intervals post-infection, e.g., 1 and 5 hours, mice were dosed subcutaneously with graded doses of the new dipeptide, antibiotic and a combination thereof. The number of mice surviving each treatment for 7 days post-infection was observed and the $CD_{50}$ is calculated. The results using D-cycloserine as an example of the antiobiotic and representative fluorinated dipeptides are shown in Table II, using *Staph. aureus* (Smith) as the infecting organism. The values are listed in mg./kg.

TABLE II

| Example | Peptide | Cycloserine | Peptide + Cycloserine |
|---|---|---|---|
| 1 | 9.4 | 8.4 | 1.9 + 0.18 |

TABLE II-continued

| Example | Peptide | Cycloserine | Peptide + Cycloserine |
|---|---|---|---|
| 2 | 75–150 | 25 | 4–9 + 0.4–0.9 |

The compounds of the present invention can be administered intramuscularly, orally, subcutaneously or intravenously. Sterile, liquid dosage forms can easily be prepared for parenteral administration by dissolving the above dipeptide in the form of a water-soluble, nontoxic salt in isotonic sodium chloride solutions containing optional buffers, stabilizers, and/or preservatives. Liquid oral dosage forms in the form of elixirs, syrups or suspensions can be made in standard fashion, also optionally containing the above additives together with coloring or flavoring agents.

Solid dosage forms for oral administration include tablets, capsules, pills and wafers. For these dosage forms, the usual solid diluents are used where required. Capsules can be filled with undiluted powdered or granulated crystals of the new compounds. For tablets, the following standard procedure may be used:

About one-half of 50 g. of cornstarch is milled together with 50 g. of the above dipeptide and 220 g. of calcium phosphate dibasic dihydrate. This blend is milled until homogenous and passed through a 40-mesh screen. The remaining portion of the cornstarch is granulated with water, heated and mixed with the above drug blend in a hot air oven at 50° C. and sifted through a 16-mesh screen. These granules are then mixed with 16 g. of talcum powder, 4 g. of magnesium stearate and 0.8 g. of combined coloring and flavoring additives. The mixture is blended to homogeneity, passed through a 30-mesh screen and blended for another 15 minutes. This blend is compressed into tablets weighing approximately 350 mg. using a 9/32" standard convex punch resulting in tablets of a hardness of 7–9 with each tablet containing 50 mg. of the drug. In a similar fashion, tablets weighing 600 mg. containing 250 mg. of drug can be prepared, preferably in a tableting machine producing bisected tablets.

While the above examples are directed to the peptides and their esters, their acid addition salts can readily be prepared and used in the same known fashion. The nontoxic salts useful as antibacterials include primarily the hydrochloride, phosphate, sulfate, acetate, succinate and citrate.

As will be seen from the above examples, the current dipeptides are antibacterially active in warmblooded animals. Against certain bacteria, the new dipeptides are powerful synergists for known antibacterials, enabling the use of the latter in quantities of only a small fraction of its curative dose. In particular, by combining the current dipeptide with a medicinally useful antibiotic in a weight ratio of 1:1 to 10:1, excellent antibacterial synergism is observed. While the demonstrated synergistic results above are based on the use of a specific antibiotic, it will be understood that other antiobiotics including pencillins such as carbenicillin, cephalosporins such as cephalothin, streptomycin, erythromycin, tetracyclin, etc. can be combined with the new peptides to obtain better results than with such antibiotics alone. The dipeptides can be used in the usual form, as the corresponding loweralkyl esters thereof and/or as nontoxic addition salts thereof. The dipeptides wherein R is a protective group are intermediates for the preparation of the dipeptides wherein R is hydrogen and in some instances have useful pharmacological effects as precursors for $N^\alpha$-unprotected dipeptides or dipeptide esters of this invention.

We claim:

1. A dipeptide of the formula

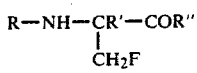

wherein the shown aminoacid is in the D-configuration, R is hydrogen or an easily removable, protective group, R' is hydrogen or deuterium and R" is a protein derived aminoacid in the L-configuration, or the corresponding loweralkyl esters, or a nontoxic acid addition salt thereof.

2. The dipeptide of claim 1 wherein R and R' are hydrogen.
3. The dipeptide of claim 2 wherein R" is alanine.
4. The dipeptide of claim 2 wherein R" is valine.
5. The dipeptide of claim 2 wherein R" is leucine.
6. The dipeptide of claim 2 wherein R" is glutamic acid.
7. The dipeptide of claim 2 wherein R" is α-aminoisobutyric acid.
8. The dipeptide of claim 2 wherein R" is phenylalanine.

* * * * *